(12) United States Patent
Feng (10) Patent No.: US 11,613,724 B2
(45) Date of Patent: Mar. 28, 2023

(54) SINGLE-USE BIOREACTOR SENSOR INTERFACE

(71) Applicant: Rosemount Inc., Shakopee, MN (US)

(72) Inventor: Chang-Dong Feng, Long Beach, CA (US)

(73) Assignee: Rosemount Inc., Shakopee, MN (US)

( * ) Notice: Subject to any disclaimer, the term of this patent is extended or adjusted under 35 U.S.C. 154(b) by 0 days.

(21) Appl. No.: 15/278,766

(22) Filed: Sep. 28, 2016

(65) Prior Publication Data
US 2017/0166852 A1    Jun. 15, 2017

Related U.S. Application Data

(60) Provisional application No. 62/265,819, filed on Dec. 10, 2015.

(51) Int. Cl.
| | |
|---|---|
| *C12M 3/00* | (2006.01) |
| *C12M 1/00* | (2006.01) |
| *C12M 1/12* | (2006.01) |
| *B29C 65/56* | (2006.01) |
| *B29C 65/00* | (2006.01) |

(Continued)

(52) U.S. Cl.
CPC ........... *C12M 23/28* (2013.01); *B29C 65/562* (2013.01); *B29C 66/522* (2013.01); *C12M 23/00* (2013.01); *C12M 23/38* (2013.01); *C12M 37/04* (2013.01); *C12M 41/26* (2013.01); *C12M 41/34* (2013.01); *C12M 41/40* (2013.01); *B29K 2021/00* (2013.01); *B29L 2031/34* (2013.01)

(58) Field of Classification Search
CPC ..................................................... C12M 23/28
USPC .......................................................... 435/287.5
See application file for complete search history.

(56) References Cited

U.S. PATENT DOCUMENTS

| | | | | |
|---|---|---|---|---|
| 4,577,110 A | * | 3/1986 | MacBride ............ | G01N 21/645 250/461.2 |
| 4,803,365 A | * | 2/1989 | Krause ................... | G01N 21/64 250/432 R |

(Continued)

FOREIGN PATENT DOCUMENTS

| | | |
|---|---|---|
| WO | 2010017519 A1 | 2/2010 |
| WO | 2013063550 A1 | 5/2013 |

OTHER PUBLICATIONS

"Selecting the Right Hose Barb—What You Need to Know", Mar. 18, 2014, Holland Applied Technologies, web article accessed at https://hollandaptblog.com/2014/03/18/selecting-the-right-hose-barb-what-you-need-to-know/ (Year: 2014).*

(Continued)

*Primary Examiner* — Nathan A Bowers
(74) *Attorney, Agent, or Firm* — Christopher R. Christenson; Kelly, Holt & Christenson, P.L.L.C.

(57) ABSTRACT

A bioreactor sensing system is presented. The bioreactor sensing system comprises a bioreaction vessel. The bioreaction vessel comprises an aperture configured to provide an interface for monitoring contents within the bioreaction vessel. The bioreaction vessel also comprises a port coupled to the bioreaction vessel proximate the aperture. The bioreactor sensing system also comprises a sensing device disposed at least partially within the port such that a sensing element is exposed to the contents. The bioreactor sensing system also comprises an external seal configured to be applied over a portion of the sensing device and a portion of the port.

4 Claims, 6 Drawing Sheets

(51) Int. Cl.
*C12M 1/34* (2006.01)
*B29K 21/00* (2006.01)
*B29L 31/34* (2006.01)

(56) References Cited

U.S. PATENT DOCUMENTS

| | | | |
|---|---|---|---|
| 5,350,080 A * | 9/1994 | Brown | B67D 7/0288 |
| | | | 215/247 |
| 7,832,296 B2 | 11/2010 | Klees et al. | |
| 7,924,017 B2 | 4/2011 | Ammann et al. | |
| 7,992,846 B2 | 8/2011 | Terentiev et al. | |
| 8,123,397 B2 | 2/2012 | Baumfalk et al. | |
| 8,252,582 B2 | 8/2012 | Baumfalk et al. | |
| 8,550,439 B2 | 10/2013 | Terentiev et al. | |
| 8,640,560 B2 | 2/2014 | Burke | |
| 8,673,624 B2 | 3/2014 | Loebbert et al. | |
| 8,708,319 B2 | 4/2014 | Terentiev et al. | |
| 8,828,202 B2 | 9/2014 | Feng | |
| 9,103,703 B2 | 8/2015 | Baumfalk et al. | |
| 2004/0027912 A1 | 2/2004 | Bibbo et al. | |
| 2005/0163667 A1 | 7/2005 | Krause | |
| 2010/0255526 A1 * | 10/2010 | Braet | C12M 23/14 |
| | | | 435/29 |
| 2012/0240686 A1 | 9/2012 | Blomberg et al. | |
| 2012/0244609 A1 | 9/2012 | Selker et al. | |
| 2013/0145818 A1 | 6/2013 | Allgauer et al. | |
| 2014/0260712 A1 * | 9/2014 | Damren | G01D 11/24 |
| | | | 73/866.5 |
| 2014/0348385 A1 | 11/2014 | Erdenberger | |
| 2015/0030514 A1 | 1/2015 | Feltham | |
| 2015/0132840 A1 * | 5/2015 | Arnold | C12M 23/42 |
| | | | 156/60 |
| 2015/0198549 A1 * | 7/2015 | Kjar | G01N 27/02 |
| | | | 435/3 |

OTHER PUBLICATIONS

Screenshot of Northwest Hydra-Line hose barb fittings product page cached by Internet Archive on Feb. 22, 2015, url at http://northwesthydraline.com/fittings-adapters-couplers/home.php?cat=249 (Year: 2015).*
International Search Report and Written Opinion for PCT/US2016/064125, dated Mar. 13, 2017, 16 pages.
Extended European Search Report dated May 29, 2019, for European Patent Application No. 16873609.8, 7 pages.
First Chinese Office Action dated Jun. 24, 2020 for Chinese patent application No. 201611127141.5, 12 pages including English translation.
Second Chinese Office Action dated Dec. 15, 2020 for Chinese patent application No. 201611127141.5, 18 pages including English translation.
Chinese Rejection Decision dated Mar. 11, 2021 for Chinese patent application No. 201611127141.5, 16 pages including English translation.

* cited by examiner

SINGLE-USE BIOREACTOR SENSOR INTERFACE

CROSS-REFERENCE TO RELATED APPLICATIONS

The present application is based on and claims the benefit of U.S. Provisional Patent Application Ser. No. 62/265,819 filed Dec. 10, 2015, the content of which is hereby incorporated by reference in its entirety.

BACKGROUND

Bioreactors support biological reactions for many important applications, including cell culture, fermentation, etc. Biological reactions can be susceptible to changes in temperature, pressure, pH, and other. Additionally, as the biological reaction progresses, the reaction itself may change various parameters within the bioreaction vessel, such as dissolved oxygen content and/or pH. Accordingly, it may be important to monitor one or more process variables over time to track the progress of the biological reaction.

The life sciences industry is moving away from large, capital intensive facilities made of stainless steel with large clean in place (CIP) infrastructure and toward smaller facilities utilizing polymer-based bags or containers functioning as single-use bioreactors. A single-use bioreactor bag can be used one and then disposed. Using single-use bioreactors can significantly reduce the capital cost required for a plant. For example, in existing facilities using stainless steel CIP infrastructure, up to 90% of operating costs may be related to CIP infrastructure, including high-end instrumentation designed to withstand a steam cleaning cycle. By moving to disposable single-use bioreactor bags, the CIP portion of capital costs can be eliminated, facilities can be flexible and much smaller, which, in turn, allows the production of smaller batches that are needed, for example, for more targeted drug therapies and other small scale applications.

SUMMARY

A bioreactor sensing system is presented. The bioreactor sensing system comprises a bioreaction vessel. The bioreaction vessel comprises an aperture configured to provide an interface for monitoring contents within the bioreaction vessel. The bioreaction vessel also comprises a port coupled to the bioreaction vessel proximate the aperture. The bioreactor sensing system also comprises a sensing device disposed at least partially within the port such that a sensing clement is exposed to the contents. The bioreactor sensing system also comprises an external seal configured to be applied over a portion of the sensing device and a portion of the port.

DETAILED DESCRIPTION OF ILLUSTRATIVE EMBODIMENTS

Single-use bioreactors may have one or more interfaces configured for attaching sensor devices capable of monitoring process variables as a reaction progresses. An instrumentation interface that facilitates the use and adoption of disposable, single-use bioreaction techniques, while providing a reliable seal between instrumentation and the bioreactor would be a significant benefit to the life sciences industry.

Figure 1:
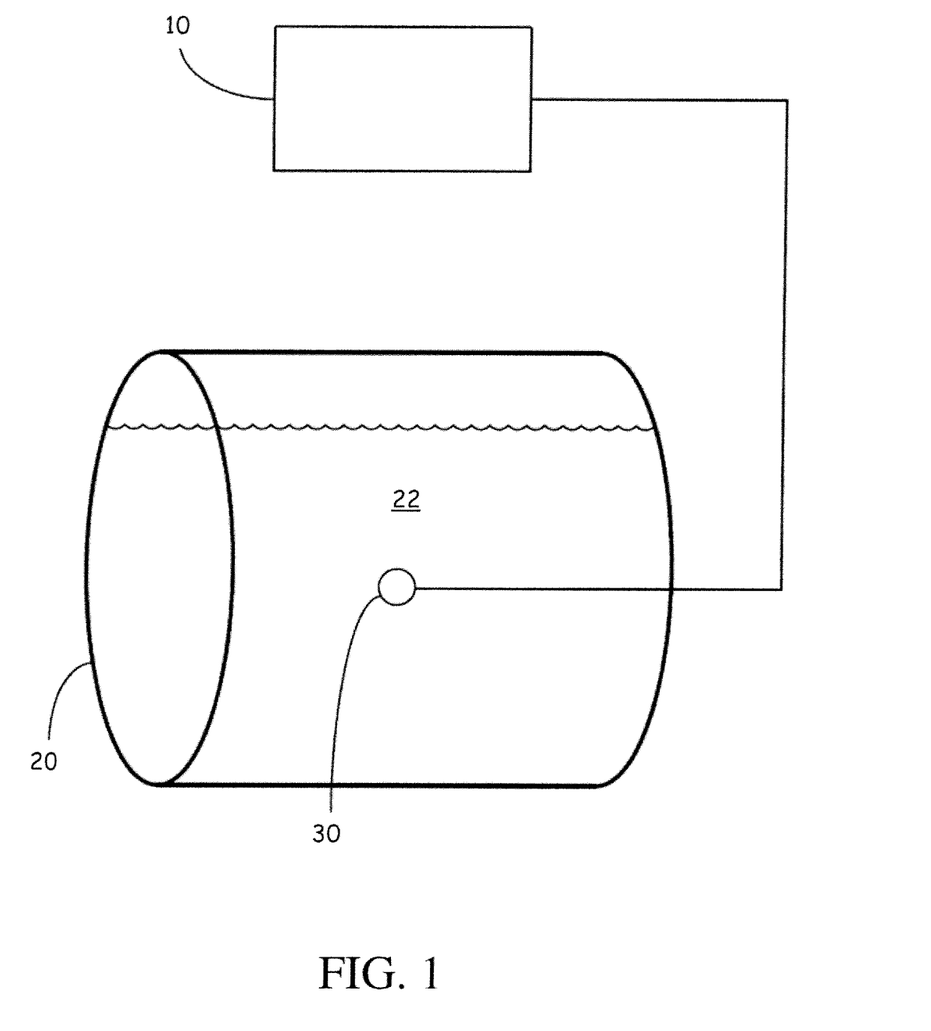
FIG. 1 is a diagrammatic view of a single-use bioreactor with which embodiments of the present invention are particularly useful.

FIG. 1 is a diagrammatic view of a single-use bioreactor with which embodiments of the present invention are particularly useful. A sensor device 30 may be useful to measure a characteristic of a biological specimen within a single-use bioreactor 20, for example pressure, temperature, pH, dissolved oxygen, etc. Sensor 30 may be mounted to a single-use bioreactor 20 and disposed to provide an electrical indication relative to a parameter of interest to a specimen 22 located within bioreactor 20. Sensor 30 is coupled to a suitable analyzer that provides a read out and/or other suitable indication of the parameter of interest with respect to specimen 22.

In single-use bioreactor applications, various sensor devices, for example sensor 30, may be integrated or otherwise coupled to a bioreactor bag. In accordance with embodiments described herein, a mechanical interface is provided between a sensor and a bioreactor. The mechanical interface may facilitate installation of the sensor within a port. The mechanical interface may also provide a high confidence of integrity. The mechanical interface may, in one embodiment, comprise a seal that prevents leaking of bioreactor fluid into the environment, and contamination by the environment of the bioreaction material. In one embodiment, the mechanical interface at least partially overlaps with a body of the sensor and/or least partially overlaps with a sensor-receiving port on the bioreactor. The use of an external seal may provide additional benefits over current systems relying on internal sealing mechanisms.

Figure 2A:
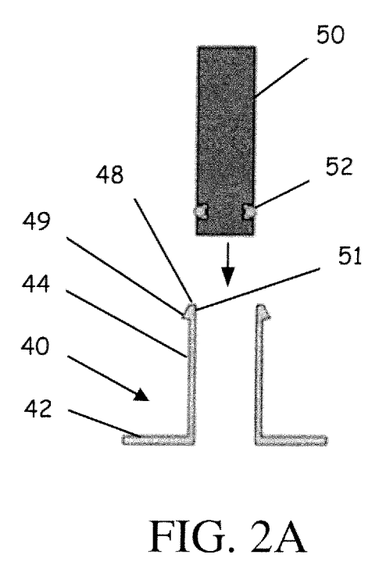
FIGS. 2A and 2B are diagrammatic views of a sensor coupled to a single-use bioreactor bag.
Figure 2B:
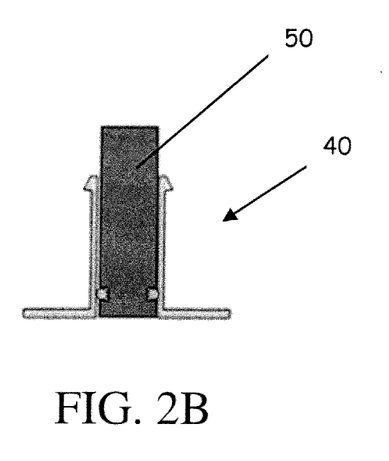

FIGS. 2A and 2B are diagrammatic views illustrating one way in which sensor devices currently couple to single-use bioreactor bags with a port 40. As shown in FIG. 2A, a single-use bioreactor bag commonly has what is referred to as a "barbed port." Barbed port 40 generally comprises a circular flange 42 that meets a cylindrical side wall 44 at an approximate right angle 46. Disposed at a distal end 48 of cylindrical side wall 44 is a hose barb 49 configured to interfere with a deformable side wall of a hose, such as a rubber or an elastomeric hose. Barbed ports 40 are common on single-use bioreactors to accommodate hoses coupled to the bioreactor.

Flange 42 may he attached to an aperture in a bioreactor bag in any suitable manner, such as ultrasonic welding, for example, or by using any other suitable methods. Flange 42 may be disposed within a bioreactor such that wall 44 passes through an aperture in the bioreactor bag. Flange 42 may also be coupled to an outside surface of the bioreactor bag such that cylindrical side wall 44 doses not pass through an aperture in the bioreactor bag. Therefore, barbed ports 40 are significantly useful, and provide flexible coupling options for tubing to the single-use bioreactors. It is desired that any external sealing mechanism be compatible, therefore, with existing barbed ports.

Currently, sensor devices, such as sensor device 50, are designed to be placed within barbed ports of a single-use bioreactor bag, such as port 40. The outside diameter of sensor 50 is sized such that it can fit within an inside diameter 51 of cylindrical side wall 44. An O-ring 52 is configured to engage an inside diameter 51 of cylindrical side wall 44, such that sensor device 50 is sealed within barbed port 40.

Sensor 50 may comprise any suitable sensing device configured to provide an electrical indication relative to a parameter of interest of the biological sample within the bioreactor bag. Such sensors can include temperature sensors, pressure sensors, dissolved oxygen sensors, carbon dioxide sensors, conductivity sensors, pH sensors, colorimetric sensors, or any other suitable sensors configured to detect a parameter of interest. When sensor 50 is properly mounted within cylindrical side wall 44, the assembly may be as shown in FIG. 2B. However, it has been discovered that the interior surface of a cylindrical side wall 44 may not have suitable quality control in order to reliably form a seal using O-ring 52. The primary design characteristic of a barbed port 40 is to couple to a segment of tubing, and allow fluid flow therethrough. To use the inside surface of cylindrical sidewall 44 to seal against a sensor 50, using only an O-ring 52, may not achieve a suitably robust fluidic and/or mechanical seal for all applications. For example, if there is a scratch on inside diameter 51 of cylindrical side wall 44, there is a risk of leaking fluid through the scratch after sensor device 50 is mounted therein. An external seal may provide a more reliable and more robust seal.

In one embodiment, a sensor coupling configuration may comprise use of an external seal to prevent fluid from passing through either of the sensor 50 or the cylindrical side wall 44. Such an external seal may be used alone to mechanically seal a sensor to a bioreactor, or be used in addition to an internal sealing mechanism as described with regard to FIGS. 2A and 2B, in the event a redundant seal is desired.

Figure 3:
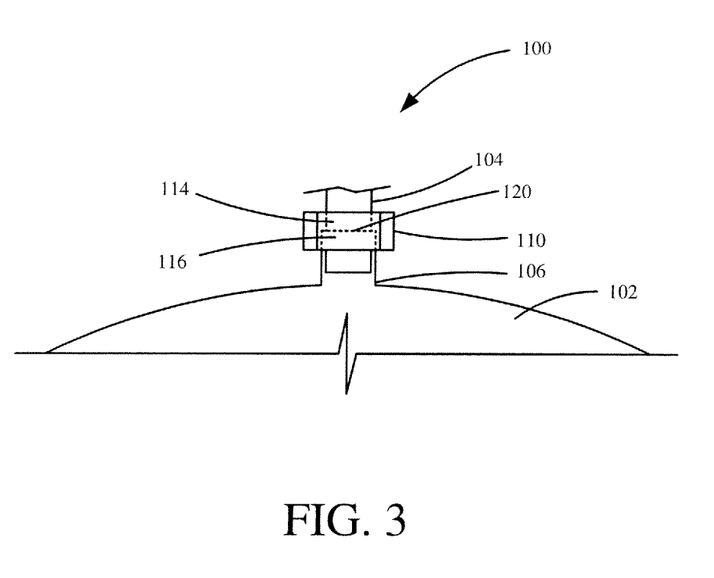
FIG. 3 is a diagrammatic view of a scaled coupling between a sensor and a bioreactor port in accordance with one embodiment of the present invention.

FIG. 3 is a diagrammatic view of a sealed coupling between a sensor and a bioreactor port in accordance with one embodiment of the present invention. An external seal, in one embodiment, may provide additional protection to current sensor-bioreactor coupling configurations. For example, the external seal may be placed over the sensor-port assembly illustrated in FIG. 2B. In another embodiment, an external seal is used without an additional sealing mechanism between the sensor and the port.

An external seal may support the use of a wide range of sensor bioreactor bag configurations. An external seal may also provide a more reliable and more robust seal than, for example, an O-ring between the sensor and the port. It may be desired to isolate a reaction mixture inside bioreactor 102 from an environment 100 outside bioreactor 102. In one embodiment, a seal 110 may be placed at an interface or coupling between sensor 104 and sensor port 106 in order to reinforce, or create, a barrier between a reaction mixture and environment 100.

In one embodiment, sensor 104 has an outer diameter smaller than, and configured to fit within, an interior diameter of a receiving sensor port 106. The sensor port 106 may be formed of a material with some elasticity, such that it can more easily receive sensor 104 without significant gaps. In one embodiment, at least a portion of sensor 104 is configured to fit within sensor port 106. A port coupling portion 116 is configured to receive, and couple to, a sensor coupling portion 114 at a junction 120. Port portion 116 and sensor portion 114 are configured to fit together, for example, with corresponding shapes.

In one embodiment, seal 110 is configured to overlap at least a portion of sensor 104 and a portion of port 106, such that it spans junction 120. Sensor portion 114 physically interfaces with port portion 116 at junction 120. In one embodiment, sensor portion 114 physically couples to port portion 116, for example through the interlocking of corresponding features. In one embodiment, junction 120 extends substantially along the entire circumference of sensor 104. There may be different possible shapes and configurations for sensor coupling portion 114 and port coupling portion 116 along junction 120. In one embodiment, the shape of sensor portion 114 matches the shape of port portion 116.

Figure 4A:
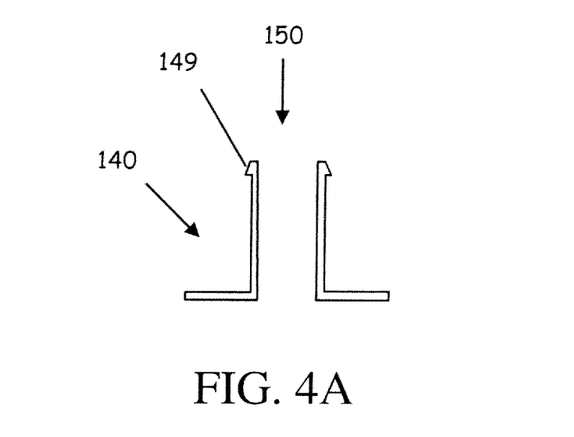
FIGS. 4A-4D are diagrammatic views of a sensor coupling to a port on a bioreactor in accordance with an embodiment of the present invention.
Figure 4B:
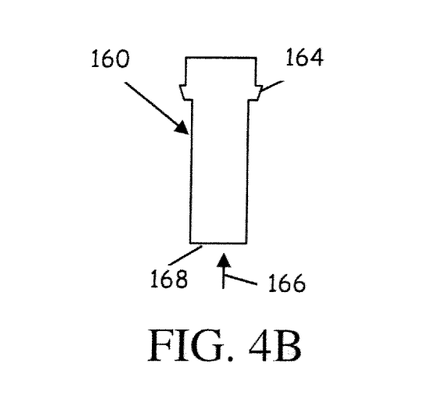

FIGS. 4A-4D illustrate a sensor coupling to a port on a bioreactor in accordance with an embodiment of the present invention. As shown in FIG. 4A, in one embodiment, a barbed port 140 comprises one barb 149 extending along a circumference of port 140. In one embodiment, barb 149 is located substantially at an edge of port 140. However, port 140 may comprise multiple barbs 149, or portions of barbs 149 extending along the length of port 140, and comprise one or more portions of a circumference of port 140. In one embodiment, barb 149 is a hose barb. In one embodiment, port 140 is configured to receive sensing device 160, as shown in FIG. 4B, in the direction indicated by arrow 150. Accordingly, at least some embodiments illustrated herein require no changes to the barbed port of a single-use bioreactor. This may be useful, in order to provide a more substantial seal between sensor 160 and existing bioreactors already available on the market.

FIG. 4B illustrates a sensing device 160 with a sensing end 168 configured to sense one or more parameters associated with a reaction mixture in a bioreactor. In one embodiment, sensor 160 is cylindrical in shape, and configured to fit within an interior diameter 151 of barbed port 140. In one embodiment, sensor 160 comprises a hose barb 164, located along the length of an external surface of sensor 160. In one embodiment, barb 164 is located a distance from a sensing end 168. The distance between sensing end 168, and barb 164 may be selected to allow for sensing end 168 to be exposed to a reaction mixture when fully inserted within port 140.

Figure 4C:
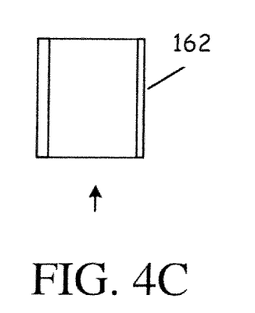
Figure 4D:
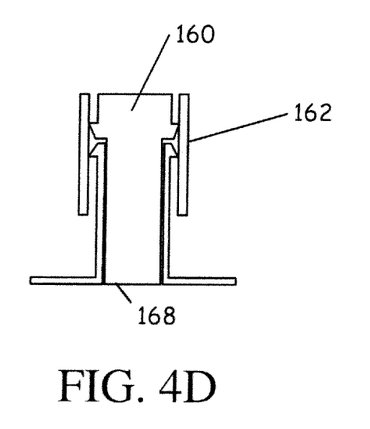

In one embodiment, sensor barb 164 is configured to cooperate with barb 149 on port 140 such that an external seal 162, shown for example in FIG. 4C, creates a robust mechanical seal between sensor 160 and port 140. In one embodiment, seal 162 comprises a flexible yet robust material. In one embodiment, seal 162 comprises elastomeric tubing. When sensing device 160 is to be mounted to barbed port 140, elastomeric tubing 162 is generally slid over the outer diameter of sensor device 160, preferably in the direction indicated by arrow 166. Seal 162 may be attached to a sensor 160 prior to insertion into port 140, in one embodiment. In another embodiment, seal 162 may be attached after sensor 160 is coupled to port 140.

in one embodiment, once elastomeric tubing 162 is positioned such that it extends both above and below barb 164, the entire sensor 160/seal 162 assembly is coupled to port 140. The sensor 160/seal 162 assembly may be configured, in one embodiment, to couple to port 140 such that barb 164 abuts barb 149, as shown in FIG. 4D, for example. Accordingly, in one embodiment, the position of hose barb 164 relative to sensing end 168 of sensing device 160 sets the relative depth of sensing end 168 within the single-use bioreactor. In the embodiments shown in FIGS. 4A-4D, sensing end 168 is substantially flush with the inside wall portion of barbed port 40. However, other desired depths of sensing end 168 are also envisioned. For example, in some embodiments it may be beneficial for sensing end 168 to extend substantially within single-use bioreactor in order to interact with a reaction mixture therein.

In at least one embodiment, for example as shown in FIG. 4D, barb 164 has opposite directional orientation from barb 149. Such opposing directionality provides that sensor 160/seal 162 assembly, when slide along the direction indicated by arrow 150, will stop when in contact with barb 149. In one embodiment, when in place, sensor 160/seal 162 generates a robust mechanical and fluidic seal with port 140. However, it is expressly contemplated that embodiments can be practiced where barbs 149 and 164 have substantially the same directionality. Additionally, while embodiments shown in FIGS. 4A and 4B illustrate a single barb portion 149 on port 140, and barb portion 164 on sensor 160, each of which can, in other embodiments, include multiple barb portions. Further still, tubing 160 may comprise any suitable polymeric material that can deform sufficiently and bias itself against hose barb portions 149 and 164 to generate a high confidence seal between the barbed port and the sensor device.

Figure 5:
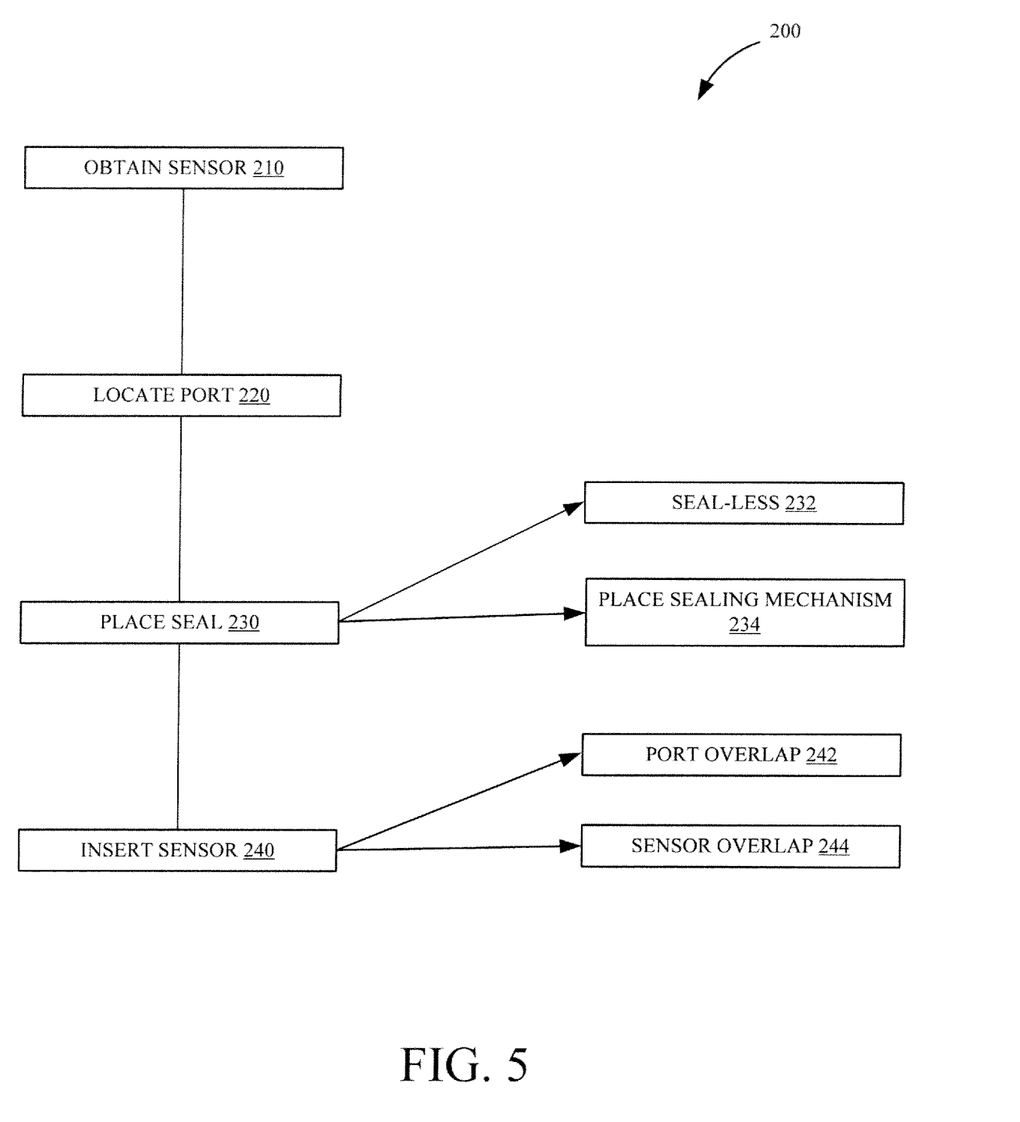
FIG. 5 is a flow diagram of a method of scaling a sensor to a bioreactor port in accordance with an embodiment of the present invention.

FIG. 5 is a flow diagram of one method of sealing a sensor to a bioreactor port in accordance with one embodiment of the present invention. Method 200, as shown in FIG. 5, illustrates one exemplary method for placing a robust seal between a bioreactor port and an exterior environment. In one embodiment, the bioreactor is a single-use bioreactor with one or more ports configured to receive one or more sensors to monitor one or more process variables. In one embodiment, the bioreactor bag has a barbed sensor port, such as that illustrated in FIGS. 4A-4D. However, other port configurations capable of coupling with a sensor are also contemplated. For example, in one embodiment, a different port configuration may be used that can sufficiently both receive a sensing element and a sealing element.

In block 210, a sensing element is obtained. The sensing element may be a pressure sensor, a temperature sensor, or any other appropriate sensor to detect any appropriate parameter to monitor an ongoing reaction within a bioreactor. In one embodiment, the sensor obtained in block 210 includes a coupling feature configured to allow for a mechanical coupling to the port on the bioreactor bag. In one embodiment, the bioreactor bag comprises a barbed port and the sensor also comprises corresponding barbs. The barbs on both the sensor and the port may be oriented in the same direction or an opposing direction.

In block 220, a port is located for interfacing with a sensing device. A bioreactor bag may comprise one or more ports, and different sensors may be more advantageously placed in different ports, based on the need to monitor different process variables. In block 220, a port is located for coupling to a sensing element. The port is located such that it has features configured to mechanically couple to the selected sensing element.

In block 230, a sensing element is positioned within port of a bioreactor bag. This may include inserting, or sliding, the sensor into the port. Additionally, the sensor may include its own sealing mechanism. In such an embodiment, as indicated by block 234, it may be necessary to place the sealing mechanism as desired. For example, in one embodiment, a sensing element with an O-ring seal may be placed within a port as a secondary seal. However, in another embodiment, the sensing element does not comprise a sealing element, as indicated in block 232, and positioning the sensing element includes moving the sensing element into place within a port prior to placing the sealing element. In one embodiment, this may include sliding the sensing element along an interior edge of the selected port until the sensing element is exposed to a reaction mixture. In one embodiment, the sensor is in place when a feature along an exterior edge of the sensor couples to, or abuts, a corresponding feature along an edge of the port. For example, in one embodiment, both the sensor and the port comprise barb elements.

In block 240, an exterior seal is provided. As indicated in FIG. 5, the sensor is first moved into place within the seal, and the seal/sensor assembly is then coupled to the port. However, it is expressly contemplated that a seal may be provided after a sensor is actuated within a port. In one embodiment, the seal is configured to at least partially overlap with a port, as indicated in block 242 and/or at least partially overlap with a portion of the sensor, as indicated in block 244. In one embodiment, the seal is configured to substantially cover equal portions of the sensor and the port.

Although the present invention has been described with reference to preferred embodiments, workers skilled in the art will recognize that changes may be made in form and detail without departing from the spirit and scope of the invention.

What is claimed is:

1. A method of sealably coupling an analytic sensor to a bioreactor, the method comprising:
    locating a port on the bioreactor, that is configured to receive a sensing element of the analytic sensor, the port having a port hose barb;
    providing the analytic sensor having a shape to be received into the port, the analytic sensor having a sensor hose barb; sliding elastomeric seal over the sensor hose barb; and
    inserting the analytic sensor into the port such that the sensing element is exposed to an interior of the bioreactor, wherein the analytic sensor is inserted until the elastomeric seal slides over the port hose barb.

2. The method of claim 1, wherein a depth Of the sensing element within the port is determined by the position of the sensor hose barb on the sensor.

3. The method of claim 1, wherein the sensor hose barb has a directionality opposed to the port hose barb.

4. The method of claim 1, wherein sliding the elastomeric seal over the sensor hose barb occurs prior to inserting the analytic sensor into the port.

* * * * *